United States Patent
Amick et al.

(10) Patent No.: US 12,089,593 B2
(45) Date of Patent: *Sep. 17, 2024

(54) COMPOSITIONS AND METHODS FOR TREATING AND PREVENTING DUST MITE INFESTATION

(71) Applicant: EVOLVA SA, Reinach (CH)

(72) Inventors: Jean Davin Amick, Lexington, KY (US); Bryan N. Julien, Lexington, KY (US)

(73) Assignee: DANSTAR FERMENT AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/086,494

(22) PCT Filed: Mar. 24, 2017

(86) PCT No.: PCT/EP2017/057124
§ 371 (c)(1),
(2) Date: Sep. 19, 2018

(87) PCT Pub. No.: WO2017/162877
PCT Pub. Date: Sep. 28, 2017

(65) Prior Publication Data
US 2019/0090482 A1    Mar. 28, 2019

Related U.S. Application Data

(60) Provisional application No. 62/341,321, filed on May 25, 2016, provisional application No. 62/313,001, filed on Mar. 24, 2016.

(51) Int. Cl.
*A01N 35/06* (2006.01)
*A61L 2/10* (2006.01)
*A61L 2/18* (2006.01)
*B08B 5/04* (2006.01)

(52) U.S. Cl.
CPC .............. *A01N 35/06* (2013.01); *A61L 2/10* (2013.01); *A61L 2/18* (2013.01); *B08B 5/04* (2013.01)

(58) Field of Classification Search
CPC .................................. A01N 25/06; A01P 7/04
See application file for complete search history.

(56) References Cited

U.S. PATENT DOCUMENTS

| | | |
|---|---|---|
| 4,800,196 A | 1/1989 | Nomura et al. |
| 5,317,041 A | 5/1994 | Chapman et al. |
| 5,847,226 A | 12/1998 | Muller et al. |
| 5,916,917 A * | 6/1999 | Suh .................. A01N 37/10 514/544 |
| 6,107,341 A | 8/2000 | Hansen et al. |
| 6,124,275 A * | 9/2000 | Emerson .............. A01N 37/02 514/159 |
| 6,531,303 B1 | 3/2003 | Millis et al. |
| 6,685,948 B1 | 2/2004 | Zeng et al. |
| 6,689,593 B2 | 2/2004 | Millis et al. |
| 6,808,717 B1 | 10/2004 | Bale |
| 7,129,271 B2 | 10/2006 | Maupin |
| 7,442,785 B2 | 10/2008 | Chappell et al. |
| 8,551,510 B2 | 10/2013 | Bedoukian |
| 11,191,266 B2 | 12/2021 | Amick et al. |
| 11,737,459 B2 * | 8/2023 | Amick ................ A01N 35/06 504/101 |
| 2004/0249219 A1 | 12/2004 | Saucy et al. |
| 2005/0176818 A1 | 8/2005 | Maupin et al. |
| 2005/0187289 A1 | 8/2005 | Dolan et al. |
| 2007/0192986 A1 * | 8/2007 | Garcia ...................... A47L 9/00 15/339 |
| 2010/0151519 A1 | 6/2010 | Julien et al. |
| 2012/0246767 A1 | 9/2012 | Amick et al. |
| 2015/0007368 A1 | 1/2015 | Saran et al. |
| 2015/0250166 A1 | 9/2015 | Goldblum et al. |
| 2019/0098897 A1 * | 4/2019 | Amick ................ A01N 35/06 |

FOREIGN PATENT DOCUMENTS

| | | |
|---|---|---|
| EP | 1033076 | 9/2000 |
| EP | 1083233 | 3/2001 |
| EP | 2 537 926 | 12/2012 |
| JP | H10-87409 A | 4/1998 |
| WO | WO01/28343 | 4/2001 |
| WO | WO02/50053 | 6/2002 |
| WO | WO2010/126576 | 11/2010 |
| WO | 2014/031790 A1 | 2/2014 |

OTHER PUBLICATIONS

Potter, "House Dust Mites", Cooperative Extension Service, University of Kentucky College of Agriculture, 3 pages, Jan. 2000 (Year: 2000).*
International Search Report and Written Opinion for Int. App. No. PCT/EP2017/057124, mailed Jun. 27, 2017.
Chang, J. H. et al., "Effect of Application of Benzyl Benzoate on House Dust Mite Allergen Levels," Annals of Allergy, Asthma & Immunology, 1996, vol. 77, Nr:3, pp. 187-190.
"Safety Assessment of Citrus Derived Peel Oils as Used in Cosmetics," Cosmetic Ingredient Review Expert Panel Final Report, Sep. 30, 2014: 1-31.
Gionfriddo et al. "Elimination of Furocoumarins in Bergamot Peel Oil," Perfumer & Flavorist., 29:48-52 (2004).
Maia et al. "Plant-based insect repellents: a review of their efficacy, development and testing," Malaria Journal 10: Suppl1-11 (2011).
Hartley et al., "DNA cloning using in vitro site-specific recombination," Genome Res. Nov. 2000;10(11):1788-95.

(Continued)

*Primary Examiner* — Robert T. Crow
*Assistant Examiner* — John P Nguyen
(74) *Attorney, Agent, or Firm* — Hoxie & Associates LLC

(57) ABSTRACT

Compositions comprising nootkatone, benzyl benzoate and a carrier as well as methods for treating and preventing dust mite infestations are disclosed herein.

18 Claims, 5 Drawing Sheets
Specification includes a Sequence Listing.

(56) References Cited

OTHER PUBLICATIONS

Kejlova et al., "Phototoxicity of bergamot oil assessed by in vitro techniques in combination with human patch tests." Toxicol In Vitro., 21 :1298-1303 (2007).
Limonene CASRN: 138-86-3; Toxnet Toxicology Data Network.
Takahashi et al., "Metabolic engineering of sesquiterpene metabolism in yeast," Biotechnol Bioeng. 97(1):170-81 (2007).
International Preliminary Report on Patentability for International Application No. PCT/EP2017/057124, mailed Sep. 25, 2018.
Fishel, F., Using Your Handhed Lawn and Garden Sprayer, 2009, University of Florida Institute of Food and Agricultural Sciences, pp. 1-4 (2009).
International Search Report and Written Opinion for Int. App. No. PCT/EP2017/057138, mailed Jun. 13, 2017.
Audrain et al.: "Allergy to oxidized limonene and linalool is frequent in the U.K.", British Journal of Dermatology, vol. 171, No. 2 (2014).
"Flavor & Fragrance Compendium," Bedoukian Research, 169 pages https://search.bedoukian.com/ftavorfragrance/downloads/catalog_ff.pdf.
"Orange oil" Wikipedia, Wikimedia Foundation, Nov. 29, 2019, https://en.wikipedia.org/w/index.php?title=Orange_oil&oldid=9284 74807.
Written Opinion of the International Searching Authority for PCT/EP2017/072027 dated Dec. 12, 2017, pp. 1-7.
Behle, Robert W., et al., "A Formulation to Encapsulate Nootkatone for Tick Control," Journal of Medical Entomology, 2011, vol. 48, Nr:6, pp. 1120-1127.
Bomgardner, "Nootkalone tested as a mosquito repellent" C&EN Global Enterprise (ACS Publication) (2016) vol. 94(14), p. 10.
Chen, Xu Bo et al. "Essential Oil Composition and Larvicidal Activity of Clinopodium gracile (Benth) Matsum Labiatae) Aerial Parts against the *Aedes albopictus* Mosquito" Tropical Journal of Pharmaceutical Research (2013) vol. 12(5), pp. 799-804.
Dancewicz, K., et al., "Deterrent activity of (+)-nootkatone and its derivatives towards the peach potato aphid (*Myzus persicae sulzer*)," Progress in plant protection, 2012, vol. 52, Nr:5, pp. 221-225.
Dolan, Marc C., et al., "Ability of Two Natural Products, Nootkatone and Carvacrol, to Suppress Ixodes scapularis and Amblyomma americanum (Acari: Ixodidae) in a Lyme Disease Endemic Area of New Jersey," Journal of Economic Entomology, 2009, vol. 102, Nr:6, pp. 2316-2324.
Flor-Weiler, Lina B., et al., "Susceptibility of Four Tick Species, *Amblyomma americanum, Dermacentor variabilis, Xodes scapularis,* and *Rhipicephalus sanguineus* (Acari: Ixodidae), to Nootkatone From Essential Oil of Grapefruit," Journal of Medical Entomology, 2011, vol. 48, Nr.2, pp. 322-326.
Hamdan et al. "Anti-inflammatory, insecticidal and antimicrobial activities and chemical composition of the essential oils of different plant organs from navel orange (*Citrus sinensis* (L.) *osbeck* var. *malesy*) grown in Egypt" Journal of Medicinal Plants Research (2013) vol. 7(18), pp. 1204-1215.
Kardarohman, et al. "Biolarvicidal of Veliver Oil and Ethanol Extract of Veliver Root Distillation Waste Veliveria zizanoides) Effectiveness toward *Aedes aegypti, culex* sp., and Anopheles sundaicus" Journal of Essential Oil-Bearing Plants (2013) vol. 16(6), pp. 749-762.
Karlberg et al., "Contact allergy to oxidized D-limonene among dermatitis patients", Contact Dermatitis, p. 201-206 (1997).
Letizia, C. S. et al., "Nootkatone," Food and Chemical Toxicology, vol. 38, Supplement 3, 2000, pp. s165-s167.
Mao, L., et al. "Vetiver oil and nootkatone effects on the growth of pea and citrus," Industrial Crops and Products,2006, vol. 23, Nr:3, pp. 327-332.
Mcallister et al., "Mode of Action for Natural Products Isolated From Essential Oils of Two Trees Is Different From Available Mosquito Adulticides" Journal of Medical Entomology (2010) vol. 47(6), pp. 1123-1126.
National Center for Biotechnology Information. PubChem Database. Limonene, CID=22311, https://pubchem.ncbi.nlm.nih.gov/compound/Limonene (accessed on Apr. 28, 2020).
Nootkatone Safety Data Sheet—Bedoukian Research 2015 at http://search.bedoukian.com/product_images/mxts/801_English_SDS_US.pdf (retrieved from the internet Dec. 29, 2019) (2015).
Nootkatone Sigma-Aldrich Product No. 74437 at https://www.sigmaaldrich.com/catalog/product/aldrich/74437?lang=en&region=US&cm_sp=Insite-_-caContent_prodMerch_gruCrossEntropy-_-prod Merch 10-1) (Retrieved from the internet Jan. 21, 2021) (2021).
International Search Report and Written Opinion for Int. App. No. PCT/EP2017/057133, mailed Jun. 14, 2017.
International Search Report and Written Opinion for Int. App. No. PCT/EP2017/057137, mailed Jun. 14, 2017.
International Search Report (ISR) for PCT/EP2017/072027 dated Dec. 12, 2017, pp. 1-5.
Jongedijk et al., "Biotechnological Production of Limonene in Microorganisms," Appl Microbiol Biotechnol., vol. 100, p. 2927-2938, (2016).

\* cited by examiner

Name: Limonene
Formula: C10H16
MW: 136  Exact Mass: 136.1252  CAS#: 138-86-3  ID#: 443  DB: ffnsc2
Other DBs: None
Contributor: Prof. L. Mondello (Chromaleont s.r.l./Univ. Messina, Italy)
Comment: WileyID="LM_FFNSC14_443" RI1="1030 (SLB-5MS)" RI2
10 largest peaks:
68 999 | 67 703 | 93 631 | 79 327 | 94 283
41 235 | 92 219 | 107 187 | 53 179 | 121 179

Synonyms:
1. Cyclohexene, 1-methyl-4-(1-methylethenyl)-

Estimated non-polar retention index (n-alkane scale)
Value: 1018 u
Confidence interval (Hydrocarbons): 39(50%) 167(95%) u Retention index
1. Value: 1020 u
Column Type: Capillary
Column Class: Standard non-polar
Active Phase: RTX-1
Column Length: 60 m

Figure 4 (Cont.)

COMPOSITIONS AND METHODS FOR TREATING AND PREVENTING DUST MITE INFESTATION

CROSS-REFERENCE TO RELATED APPLICATIONS

The present application is a U.S. National Phase Application pursuant to 35 U.S.C. § 371 of International Application No. PCT/EP2017/057124 filed Mar. 24, 2017, which claims priority to U.S. Provisional Patent Application No. 62/341,321, filed May 25, 2016, and U.S. Provisional Patent Application No. 62/313,001, filed Mar. 24, 2016. The entirety of the disclosure of each of these applications is hereby incorporated by reference into the present application.

BACKGROUND OF THE INVENTION

Field of the Invention

This disclosure relates to the use of nootkatone-containing compositions to kill and/or repel house dust mites.

Description of Related Art

The North American house dust mite (dust mite) *Dermatophagoides farinae* and the European dust mite *Dermatophagoides pteronyssinus* are closely related, and thanks to ease of modern travel, are each now found in the traditional territory of the other species. Dust mites thrive in the indoor environments of homes, hotels, and work places. They live in mattresses, carpets, rugs, furniture, and bedding at up to 100-500 mites per gram of dust.

Dust mites feed on organic material like shed human skin, which tends to be concentrated in lounging areas, such as mattresses, frequently used furniture, and associated carpeted areas. Additionally, dust mites particularly thrive in objects and structures that absorb and retain moisture from exhaled breath or body contact, including duvets, bedding, and especially pillows. Since many people are in bed about eight hours per day, these areas make prime habitats for dust mites.

Male dust mites live 10-19 days on average, whereas a mated female may live up to 70 days, laying 60-100 eggs and producing approximately 2,000 fecal particles and even more partially-digested, enzyme-covered dust particles. It is these enzyme-covered dust particles that are thought to cause dust mite allergies and associated asthma. Dust mites are difficult to see; therefore such dust mite-associated conditions are typically diagnosed by immunological testing.

Many studies link the presence of dust mites with occurrence of allergic rhinitis and/or asthma. The American College of Asthma, Allergy and Immunology has estimated that approximately 10 percent of Americans exhibit allergic sensitivity to dust mites, whilst the National Institute of Environmental Health Services has estimated that 18% to 30% of Americans are allergic to dust mites' waste products. There is a genetic predisposition to dust mite allergy, but sensitivity can also develop over time. Therefore, treating and preventing dust mite infestations is of particular interest to families having members suffering from or prone to breathing issues, allergies, and asthma.

Unfortunately, current options for controlling dust mites are less than ideal. For example, routine cleaning activities such as dusting and changing bed clothing remove dust and dust mites. Though, these activities also disturb dust and dust mites and increase the levels of dust mite allergens in the air.

Mattress covers impervious to dust mite penetration offer another approach to controlling dust mites. Yet, it is not possible to identify when such a cover becomes punctured or degrades to the point that mites are able to enter the interior. Further, many people find mattress covers to be uncomfortable because they do not allow the parts of the body resting on the mattress to adequately "breathe" and allow accumulation of body moisture in the bed.

Other recommended methods of reducing dust mite populations include decreasing the humidity to below about 50% and decreasing the ambient air temperature to below about 20° C. But, such strategies are rarely employed because they are considered to be less comfortable for people and have limited effect on the preferred habitats of dust mites, including such dust mite rich environments as beds, mattresses, bedding, and pillows.

Moreover, because dust mites live in human dwellings, treatment with conventional miticides, such as synthetic miticides, is counterindicated due to the likelihood of human exposure. Conventional miticides have been reported to be either toxic to humans or potentially allergenic themselves. Often, such miticides have strong chemical odors or fumes making them undesirable even when direct exposure is likely to be minimal. Therefore, in light of the prevalence and problems caused by dust mite infestation and the challenges to combating dust mites, there is a growing need for effective, environmentally friendly compositions and methodologies to prevent and treat dust mite infestations.

SUMMARY OF THE INVENTION

Provided herein are effective compositions and methods of for treating and preventing house dust mite infestations.

In a first aspect, the invention provides a method of treating or preventing dust mite infestation of a surface including applying a nootkatone-containing composition to a surface.

In a second aspect, a method of treating or preventing a dust mite infestation including (a) providing a nootkatone-containing composition, (b) optionally reducing the concentration of the nootkatone-containing composition to a working concentration with a carrier, and (c) applying the composition to a surface. In one embodiment of the second aspect, the carrier is a liquid or a powder.

In one embodiment of the first or second aspects, the surface is either the surface to be treated or a surface of a dispenser. In a further embodiment of the first or second aspects, the composition is a concentrate.

In a third aspect, the invention provides a method of treating or preventing a dust mite infestation including applying a nootkatone-containing composition to a surface by a dispenser. The dispenser concomitantly applies the composition to the surface and removes from the surface at least one of dust, dirt, dust mite food, a dust mite allergen, grease, oil, lint, animal hair, an odor, and a stain. In one embodiment of the third aspect, the dispenser is a brush, a sponge, a soft-tipped marking device with reservoir, a pressurized dispenser, an aerosol can, a roll on bottle, a mop, a dust mop, a broom, a wipe, a tissue, a duster, a duster sheet, a wet wipe, a wet pad, a vacuum rotor, a steam cleaner, a lint brush, a paint brush, a paint roller, a washing machine, or a clothes drier.

In a fourth aspect, the invention provides a method of treating or preventing a dust mite infestation including (a)

applying a nootkatone-containing composition to a surface and (b) cleaning the surface to remove at least one of dust, dirt, dust mite food, a dust mite allergen, grease, oil, lint, animal hair, an odor, and a stain. In one embodiment of the fourth aspect, step (a) is performed before step (b). In another embodiment of the fourth aspect, step (a) is first performed and a period of time is allowed to pass before step (b) is performed. In one embodiment, the period of time is a minute, an hour, a day or any multiple thereof. In a further embodiment of the fourth aspect, the method further includes (c) reapplying the nootkatone-containing composition to the surface after step (b) is performed.

In a fifth aspect, the invention provides a method of treating or preventing a dust mite infestation including (a) applying a nootkatone-containing composition to a surface and (b) treating the surface with ultraviolet (uv) light of 200-400 nm wavelength. In one embodiment of the fifth aspect, the surface is treated with uv light for a period of a minute, an hour, or a day. In another embodiment of the fifth aspect, step (b) is performed before step (a).

In a sixth aspect, the invention provides a method for reducing the potential for or severity or frequency of an allergic reaction to dust mites including (a) applying a nootkatone-containing composition to a surface and (b) cleaning the surface to remove dust mite allergens therefrom. In one embodiment of the sixth aspect, the surface is cleaned with a vacuum. For example the vacuum can be a hypoallergenic vacuum.

In a seventh aspect, the invention provides a method of treating or preventing a dust mite infestation including (a) applying a nootkatone-containing composition to a reservoir comprising an aqueous solution to form a nootkatone film on a top surface of the aqueous solution, (b) immersing an object or dust mite rich environment to be treated into the aqueous solution, and (c) at least partially enveloping the object or dust mite rich environment with the nootkatone film by removing the object or dust mite rich environment from the reservoir. In one embodiment of the seventh aspect, the object or dust mite rich environment is a pillow, a stuffed toy, a duvet, bedding, or a bed mattress.

In an eighth aspect, the invention provides a composition for treating or preventing a dust mite infestation including a) about 0.1% to about 10% wt/vol nootkatone, b) about 0.1% to about 10% wt/vol benzyl benzoate, and c) about 80% to about 99.8% carrier.

In a ninth aspect, the invention provides a kit for treating or preventing dust mite infestation of a surface including a dispenser having a nootkatone-containing composition. The dispenser is disposed within packaging. In one embodiment of the ninth aspect, the dispenser includes wet wipes. In another embodiment of the ninth aspect, the packing is a resealable, water-tight pouch.

In one embodiment according to any of the preceding aspects, the composition includes nootkatone ex valencene. In another embodiment according to any of the preceding aspects, the nootkatone is limonene-free. In a further embodiment according to any of the preceding aspects, the nootkatone is bergapten-free.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

DESCRIPTION OF DRAWINGS

The following detailed description of the embodiments of the present invention can be best understood when read in conjunction with the following drawings.

DETAILED DESCRIPTION

Figure 1:
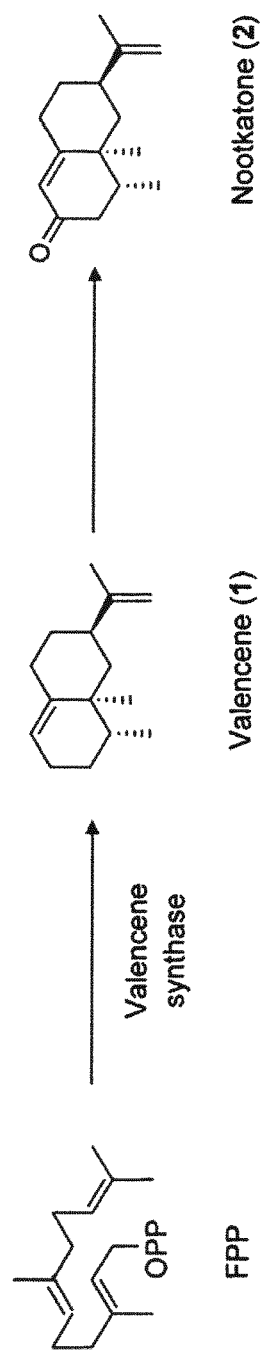
FIG. 1 illustrates a biosynthetic pathway for nootkatone.

All publications, patents and patent applications cited herein are hereby expressly incorporated by reference in their entirety for all purposes.

Before describing the present invention in detail, a number of terms will be defined. As used herein, the singular forms "a," "an," and "the" include plural referents unless the context clearly dictates otherwise. For example, reference to "an active ingredient" means one or more active ingredients.

As used herein, the term "active ingredient" refers to a chemical compound or mixture of chemical compounds that kills and/or repels a dust mite from an article of furniture, bed, sofa, chair, carpet, rug, curtain, bedding, pillow, cushion, bed sheet or duvet.

As used herein, the term "dust mite" refers to any *Dermatophagoides* species, a genus of sarcoptiform mites, including *Dermatophagoides farinae*, *Dermatophagoides microceras*, and *Dermatophagoides pteronyssinus*, but also to *Euroglyphus maynei* and further indicates a single dust mite and/or two or more dust mites of the same or different species.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree to which a quantitative representation can vary from a stated reference without resulting in a change in the basic function of the subject matter at issue.

As used herein, the term "about" refers to ±10% of any particular value.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z."

As used herein, the term "treatment of dust mite" refers to a process by which dust mites are at least one of killed, removed, or repelled from an object, a surface, or dust mite rich environment. If a primary treatment is performed to reduce dust mite population by any of applying a composition comprising nootkatone, freezing, washing at 54° C. or higher temperature, dehumidifying to 50% relative humidity or less, or physical removal of dust and dust mites therein, one or more subsequent treatments may be performed comprising application of a composition comprising nootkatone to prevent recovery of the dust mite population to levels of the prior infestation.

As used herein, the terms "dust mite infestation" and "dust mite population" are used interchangeably to refer to the presence of one or more dust mites and/or dust mite eggs and/or dust mite allergens in a given area.

As used herein, the term "dust mite allergen" refers to any part of a dust mite or anything made by a dust mite that causes an allergic reaction in a human or other animal upon exposure to the human or other animal.

As used herein, the term "subject" refers to a person or animal that has previously displayed an immune response to exposure either by inhalation or direct contact to dust mites, dust mite feces, or derivatives thereof, or dust comprising any thereof, or through deliberate exposure of the skin or a blood or tissue sample to dust mite antigens as part of an immunological test. Common symptoms displayed during an immune response to dust mite allergens include any of sneezing, a runny or stuffy nose, rhinitis, red eyes, itchy eyes, teary eyes, wheezing, coughing, tightness in the chest, shortness of breath, itchy skin, blotchy skin, eczema or a systemic inflammatory immune reaction.

As used herein, the terms "surface" or "object to be treated" or "dust mite rich environment" interchangeably refer to any surface area, subsurface area, and/or material that dust mites may attempt to traverse or inhabit as part of their foraging, breeding, or egg laying. Examples include, without limitation, carpets, floor boards, head boards, curtains, blinds, window sills, tables, desks, mantelpieces, work surfaces, doors, skirting boards, walls, the rear surface of furniture that usually rests against a wall, the interior of a cushion, pillow, or padded piece of furniture, HVAC vents and ducts, air filters, ceiling fans, furnaces, and any other object that has a surface that collects dust. Surface can be made from any material such as a natural material, a synthetic material, wood, metal, plastic, cotton, wool, silk, satin, or any woven or non-woven fabric suitable for clothing, bedding, or home furniture.

As used herein, the term "dust mite rich environment" refers to one or more environments preferred by dust mites for at least one of feeding, breeding, or egg laying and capable of harboring high concentrations of dust mites. Dust mite rich environments include sheltered areas of human and/or animal habitation or work places or any interior space frequently occupied by humans or animals, including any means of transportation or vehicle, in which dust (expressly including micro fragments of shed human and/or animal skin) may accumulate. Such dust mite rich environments include houses, hotels, motels, office buildings, vehicles, and all spaces therein and any other interior or exterior space where a dust mite population may occur. Dust mite rich environments also include materials that typically retain a more humid and/or warmer internal micro climate within their structure than the surrounding environment within the home, dwelling, or work place, and may include items of clothing, particularly items of insulated or padded clothing such as down jackets, vests, parkas, mittens, balaclavas, salopettes, etc. Examples of dust mite rich environments include but are not limited to at least one of an article of clothing or furniture, bed, sofa, chair, seat, carpet, rug, curtain, mattress, bedding, sleeping bag, pillow, cushion, comforter, stuffed toy, bed sheet, duvet, jacket, parka, hat, trousers, salopettes, and as otherwise defined herein.

As used herein, the term "room" refers to any interior space where dust mites may live. For example, "room" refers to dust mite rich environments within houses, hotels, motels, office buildings, vehicles, and all spaces therein including the surfaces and interiors of objects within the room and any other interior space where a dust mite population may occur.

As used herein the term "effective concentration" is interchangeably used with "working concentration" and refers to a concentration of an active ingredient (such as nootkatone) or other composition component that effectively achieves the desired result for the active ingredient or other composition component within the composition. For example, a contemplated effective concentration of an active ingredient in a particular composition is the concentration at which when the composition is applied to a surface, a dust mite coming into contact with the surface is repelled and/or experiences paralysis, poisoning, neuro-muscular damage, and/or death.

As used herein, the term "effectively treat" refers to direct or indirect treatment of a surface of an object that reduces a dust mite population on the surface of the object treated.

As used herein, the term "direct treatment" refers to application of a composition directly to a dust mite.

As used herein, the term "indirect treatment" refers to application of a composition directly to a surface which a dust mite subsequently contacts that causes the dust mite to be exposed to the composition.

As used herein, the terms "dust removing agent" and "surface cleaning product" are used interchangeably and refer to any object used to remove, extract, wipe, or collect dust from a subject, surface or dust mite rich environment. Examples of dust removing agents or surface cleaning products include but are not limited to at least one of a vacuum cleaner, a wet carpet cleaner, a steam cleaner, an upholstery cleaner, a duster, a feather duster, a dust mop, a wet wipe, and a wet mop pad any of which is suitable for cleaning surfaces including floors, walls, ceilings, decorative surfaces, work surfaces, mantelpieces, shelves, keyboards, ornaments, art work, carpets, rugs, plant leaves, furniture, bed frames, radiators, window sills, drapes, blinds, and vehicle interiors including buses, planes, trains and cars.

As used herein, the term "nootkatone" refers to a compound seen in FIG. 1 that may be synthesized, isolated, and purified from of a mixture of products produced in a host modified to express enzymes of the nootkatone biosynthetic pathway or that can be produced from naturally occurring sources, such as citrus plants. "Nootkatone" also refers to a mixture of chemical compounds containing or enriched for the nootkatone compound and derived from a modified host, such as a microorganism, or isolated or derived from plant extracts. "Nootkatone" further refers to derivatives and analogs thereof. For example, the nootkatone compound contemplated for use herein may be produced in vivo through expression of one or more enzymes involved in the nootkatone biosynthetic pathway in a recombinant yeast or in vitro using isolated, purified enzymes involved in the nootkatone biosynthetic pathway, such as those described in U.S. Patent Application Publication Nos. 2015/0007368 and 2012/0246767. Therefore, nootkatone as defined herein can differ chemically from other sources of nootkatone, such as extracts from plants and derivatives thereof, or may include such plant extracts and derivatives thereof.

As used herein, the term "nootkatone ex valencene" refers to nootkatone derived from oxidation of valencene that was produced by fermentation, such as by microorganisms harboring one or more valencene synthases and/or other molecules that catalyze formation of valencene. Further, nootkatone ex valencene refers to a combination of chemical compounds derived from oxidation of a valencene-containing fermentation product produced by culturing microorganisms harboring one or more valencene synthases and/or other molecules that catalyze formation of valencene. Nootkatone ex valencene can be purified to maximize the percent of nootkatone relative to other chemical compounds. For example, nootkatone ex valencene can be less than about 50%, about 50%, about 60%, about 70%, about 80%, about 90%, or about 98% nootkatone.

Overview

Disclosed herein are nootkatone-containing compositions and methods of using and dispensing the compositions that are effective at treating and preventing dust mite infestations and associated sequelae.

It is one object of some embodiments of the current invention to prevent dust mite infestation of a room by applying a nootkatone-containing composition to a surface of the room to form a repellent barrier on the surface of the room that prevents dust mites from entering or settling in the room.

It is another object of some embodiments of the current invention to treat a dust mite infestation of a room by applying a nootkatone-containing composition to a surface in a room that effectively treats dust mite infestation directly or indirectly.

It is another object of some embodiments of the current invention to provide methods and compositions containing nootkatone for inhibiting the recovery of a dust mite population after an initial treatment.

It is a further object of some embodiments of the current invention to reduce dust mite allergens in a room to reduce severity and/or frequency of allergic reactions by people and/or animals sensitive to the allergens by effectively treating a dust mite infestation of a room and/or removing dust allergens from the room.

Various methods according to some aspects of the current invention may be employed to directly or indirectly treat dust mites and surfaces with nootkatone-containing compositions to treat or prevent dust mite infestations. For example, contemplated treatment methods include adding a nootkatone-containing composition directly to a surface of a room, such as by pouring, spraying, sprinkling, misting, painting, or fogging a nootkatone-containing composition into the room.

In one embodiment, a dual cleaning/disinfecting method is contemplated. For example, a nootkatone-containing composition may be applied to a surface of a room at the same time that the surface is cleaned such as by wiping, sweeping, mopping, dusting, brushing, de-linting, sponging, vacuuming, steam cleaning, and/or scrubbing the surface. In this example, the cleaning device may be impregnated with a nootkatone-containing composition. Alternatively, conventional cleaning devices may be used to clean the room, but a nootkatone-containing composition is applied to the surface at the time of cleaning. In another embodiment, it is envisioned that a nootkatone-containing composition may be applied to the surface to be cleaned prior to cleaning the surface and/or during the cleaning and/or after the surface is cleaned.

In another embodiment, when a surface to be treated can be laundered, such as when the surface is on an item of clothing, a drapery, a comforter, a bed skirt, bed clothes, a pillow, a stuffed toy, and other cloth-based or cloth-like items, a nootkatone-containing laundry detergent may be added to the washing machine during the laundering of the surface. Similarly, when such a surface may be dried in a tumble clothes dryer, a drier sheet embedded with nootkatone-containing composition may be added to the drying cycle.

In a further embodiment, prevention of dust mite infestation of a surface is contemplated where materials used to form surfaces of a room are impregnated with a nootkatone-containing composition. For example, woven and non-woven fabrics may be impregnated with a nootkatone-containing composition prior to be used to form upholstery, furniture covers, mattress and/or bed spring covers, draperies, blinds, carpets, and/or rugs. Similarly, nootkatone-containing treatment compositions may be formulated for permanent or extended duration applications, such as paints, varnishes, floor waxes, and the like that may be applied to a surface of a room to be treated.

In one embodiment, treatment or prevention of a dust mite infestation in a room may be accomplished by placing within the room a device that serves as a dispenser of a nootkatone-containing composition. For example, the dispenser may contain a reservoir holding the nootkatone-containing composition and can emanate the composition over a period of time of seconds, minutes, hours, or days to treat or prevent a dust mite infestation. In one context, such a dispenser may be a passive dispenser, such as a passive fragrance dispenser. In another context, the dispenser may be active, such as a dispenser that releases bursts of the nootkatone-containing composition based on a timer, a signal from a motion sensor, on demand when a remote control is activated, a change of temperature, and the like. In a similar context, an active dispenser may require user interaction, such as a sachet or other reservoir that contains the nootkatone-containing composition and that can be placed within an item such as a furniture cushion, under a rug, beneath a removable furniture cover, or within a stuffed animal, such that when a user interacts with the item by sitting on, walking on, moving, hugging, etc., a burst of the nootkatone-containing composition is released into the surrounding environment.

Surfaces to be treated for dust mites can be any surface in proximity or adjacent to a dust mite rich environment, or can be any surface capable of accumulating dust comprising fragments of shed human skin.

Dust mite rich environments to be treated may comprise any thermal or sound insulation material including but not limited to feathers, down, synthetic fibers such as polyester, nylon, polyethylene terephthalate, polypropylene, mineral wool, mineral cotton, mineral fiber, glass wool, stone wool or blends or derivatives thereof or insulation derived from drawn or spun ceramics or shredded cellulose or derivatives thereof. Nootkatone-containing compositions may be coated onto the surfaces of such thermal or sound insulation or may be impregnated within the insulation. In the case of drawing or spinning insulative materials with melting points higher than the boiling point of pure nootkatone (318.6±42.0° C. at 760 mmHg), the nootkatone-containing composition may be applied after the insulative materials have cooled to below the boiling point of nootkatone, preferably below 280° C.

Compositions

Generally and without limitation, compositions contemplated herein can be in the form of an aqueous liquid, an oil-based liquid, a concentrated liquid, a gel, a foam, an emulsion, a slurry, a paint, a clear coat, a wax, a block, a pellet, a puck, a granule, a powder, a capsule, a vesicle, a microcapsule, an effervescent tablet, slow release tablet, an impregnated dissolvable sheet or film, an impregnated material, a sachet, and combinations thereof.

In certain aspects, a composition may be formulated as a liquid or aerosolizable formulation suitable for application in a spray, a mist, a fog, a roll on, a dip, a liquid detergent, a carpet cleaner, a water repellent, a stain repellent, an odor blocker, or a composition suitable for application to a human or domestic animal, such as a hand soap, body lotion, shampoo, or conditioner.

In certain aspects, a composition may be formulated to be included within or carried on a portion of material such as a tissue, pad, cloth, sponge or sheet. The material can be impregnated, immersed or coated with a liquid composition comprising nootkatone at a concentration of between 0.01-5% by volume of the liquid composition. In certain aspects, the portion of material is a disposable thin sheet of material such as a tissue, a duster sheet, a wet wipe, or a wet pad, similar to those sold under the Swiffer®, Pledge®, Windex®, Clorox® brands.

In other embodiments of the invention, compositions contemplated herein can contain an additional active ingredient, a carrier, and/or an additive and at least about 0.1%, or at least about 1%, or at least about 2%, or at least about 5%, or at least about 7.5%, or at least about 10%, or greater than about 10%, or greater than about 15%, or greater than about 20%, or greater than about 25%, or greater than about 50% by weight nootkatone. In some applications, nootkatone can be present in an amount that is greater than about 60%, about 70%, about 80%, about 90%, about 95% or about 99% by weight of the composition. In one example, the provided compositions contain nootkatone in an amount at or about 0.001% to at or about 2%, or about 0.01% to at or about 5%, or about 0.01% to at or about 75% by weight of the composition. In another example, a composition may contain nootkatone in an amount of from at or about 1% to at or about 50% by weight of the composition. In another example, a composition may contain nootkatone in an amount of from at or about 5% to at or about 40% by weight of the composition. In another example, a composition may contain nootkatone in an amount of from at or about 10% to at or about 30% by weight of the composition. In another example, a composition may contain nootkatone in an amount of from at or about 15% to at or about 25% by weight of the composition. In another example, a composition may contain nootkatone in an amount of from at or about 1% to at or about 90% by weight of the composition. In another example, a composition may contain nootkatone in an amount of about 10%, or about 15%, or about 20%, or about 25%, or about 30%, or about 50% by weight of the composition. In another example, a composition may contain nootkatone in an amount of up to about 99% or more by weight of the composition.

In one particular embodiment, a contemplated nootkatone-containing composition is provided as a concentrate. For example, a nootkatone-containing composition may be provided as a 20×, or a 10×, or a 5×, or a 3× concentrate that can be diluted by an end user with an appropriate solvent to achieve a 1× working concentration. Alternatively, a nootkatone-containing composition may be provided to an end user at a 1× working concentration. However, any concentration is contemplated for use herein. For example, compositions provided as concentrates can be used without dilution at all or may be diluted from a highly concentrated concentrate (e.g., about 20× to about 100×) to some multiple of concentration higher than 1×, such as 2×, 2.5×, 3×, etc. or can be used at a more dilute concentration, such as ½×, ¼×, ⅒×, etc.

In another embodiment, a contemplated composition can be seen in Table No. 1.

TABLE No. 1

Contemplated composition formulation.

| Ingredient | Approximate Wt. % |
| --- | --- |
| Nootkatone | 0.01-100 |
| Additional active ingredients | 0-99.9 |
| Carrier | 0-99.9 |
| Additives | 0-99.9 |

In certain embodiments, compositions contemplated herein may include nootkatone and one or more additional active ingredients. The one or more active ingredients may be effective against dust mites, such as a pesticide against dust mites, or may be effective in removing or denaturing dust mite allergens such that they cause a reduced immune response in subjects sensitive or allergic to dust mite allergens. For example, a composition including nootkatone may additionally contain at least one additional active ingredient selected from a dehydrating agent, a dehumidifying agent, a desiccant, an anhydrous salt, sodium chloride, calcium chloride, tannic acid, and benzyl benzoate.

Additional active ingredients can include those disclosed in U.S. Pat. No. 4,800,196, such as phenyl salicylate, diphenylamine, methyl beta-naphthyl ketone, coumarin, phenethyl benzoate, benzyl salicylate, phenyl benzoate, N-fluorodichloromethylthio-cyclohexene-dicarboxyimide, p-nitrobenzoic acid methyl ester, p-chlorometaxylenol, α-bromocinnamic aldehyde, 2,5-dichloro-4-bromophenol, 2-phenylphenol, sodium 2-phenylphenolate, 5-chloro-2-methyl-4-isothiazoline-3-one, 2-methyl-4-isothiazoline-3-one, and benzimidazolylmethylcarbamate. Further examples of additional active ingredients include resuethrin, phenothrin, permethrin, allethrins, tetramethrin, furamethrin, cypermethrin, decamethrin, phenvalerate, phenpropathrin, terallethrin, empenthrin and pyrethrin; pyrethroid compounds such as 1-ethynyl-2-methyl-2-pentenyl-2, 2-dimethyl-3,3-(2,2-dichlorovinyl)-cyclopropane-1-carboxylate, 1-ethynyl-2-methyl-2-pentenyl-2, 2,3, 3-tetramethylcyclopropane-1-carboxylate, α-cyano-3-phenoxybenzyl-2,2-dimethyl-3-(2,2,3-tribromomethyl)-cyclopropane-1-carboxylate; organic phosphorus compounds such as sumithion, fenthion, tetrachlorvinphos, diazinon and dichlorvos; and carbamate compounds such as those sold under the trademarks Baygon® and Sevin®.

Further examples of additional active ingredients include plant essential oil compounds or derivatives thereof. Examples include aldehyde $C_{16}$ (pure), α-terpineol, amyl cinnamic aldehyde, amyl salicylate, anisic aldehyde, benzyl alcohol, benzyl acetate, cinnamaldehyde, cinnamic alcohol, carvacrol, carveol, citral, citronellal, citronellol, p-cymene, diethyl phthalate, dimethyl salicylate, dipropylene glycol, eucalyptol (cineole) eugenol, is-eugenol, galaxolide, geraniol, guaiacol, ionone, menthol, methyl salicylate, methyl anthranilate, methyl ionone, methyl salicylate, α-phelian drene, pennyroyal oil perillaldehyde, 1- or 2-phenyl ethyl alcohol, 1- or 2-phenyl ethyl propionate, piperonal, piperonyl acetate, piperonyl alcohol, D-pulegone, terpinen-4-ol, terpinyl acetate, 4-tert butylcyclohexyl acetate, thyme oil, thymol, metabolites of trans-anethole, vanillin, and ethyl vanillin.

In some aspects, an additional active ingredient effective against dust mites can have high selective toxicity for dust mites and can be lipid-soluble so that it can be released over a period of approximately 2 months.

In one particular example, a contemplated composition includes benzyl benzoate as an additional active ingredient in an amount of about 0.1% to about 10%. For example, a contemplated composition includes about 0.1% to about 10% wt/vol nootkatone, about 0.1% to about 10% wt/vol benzyl benzoate, and about 80% to about 99.8% carrier. In another example, a contemplated composition may include a nootkatone to additional active ingredient ratio of about 1:10, or about 1:8, or about 1:6, or about 1:4, or about 1:2, or about 1:1, or about 2:1, or about 4:1, or about 6:1, or about 8:1, or about 10:1.

Additives

In other embodiments, compositions contemplated herein may include one or more additives, such as a fragrance, a preservative, a propellant, a pH buffering agent, a UV blocker, a pigment, a dye, a surfactant, an emulsifier, a solvent, a salt, an acid, a base, an emollient, and combinations thereof. Additional additives include disinfectants, dust mite attractants or chemical lures, anti-static agents to prevent dust settling, deodorants, and detergents. Contemplated disinfectants include quaternary ammonium compounds, phenol-based antimicrobial agents, and botanical oils with disinfectant properties. In one embodiment, a nootkatone-containing composition contemplated includes an organic material that a dust mite would consume.

Carrier

In other embodiments, compositions may include a carrier, such as an aqueous liquid carrier, water, a saline, a gel, an inert powder, a zeolite, a cellulosic material, a microcapsule, an alcohol such as ethanol, a hydrocarbon, a polymer, a wax, a fat, an oil, and the like. A carrier may be added to a composition in an amount of about 10%, or about 15%, or about 20%, or about 25%, or about 30%, or about 50% by weight of the composition. In some applications, a carrier can be present in an amount that is at or greater than about 60%, about 70%, about 80%, about 90%, about 95%, or about 99% by weight of the composition.

In a further embodiment, a contemplated composition may include nootkatone alone or nootkatone and only one of an additional active ingredient, a carrier, and an additive.

Additional contemplated composition formulations are disclosed in Tables No. 2-5 below. The specific formulations shown or variations thereof can be used on hard surfaces, soft surfaces, or on a subject. In some embodiments, one or more of the formulations may be favored for application in conditions where the ambient temperature is at about 30° C. or below.

TABLE No. 2

Contemplated composition formulation A.

| Ingredient | Approximate Wt. % |
|---|---|
| Nootkatone | 0.1-2 |
| Peppermint oil | 0-1 |
| Vanillin | 0-1 |
| Isopropyl alcohol | 0-99.9 |
| Butylated hydroxytoluene | 0-0.1 |
| Isopropyl myristate | 0-5 |

TABLE No. 3

Contemplated composition formulation B.

| Ingredient | Approximate Wt. % |
|---|---|
| Nootkatone | 0.1-2 |
| Isopropyl alcohol | 0-99.9 |
| Butylated hydroxytoluene | 0-0.1 |
| Grapefruit scent | 0-1 |
| Isopropyl myristate | 0-5 |
| Mineral oil | 0-5 |

TABLE No. 4

Contemplated composition formulation C.

| Ingredient | Approximate Wt. % |
|---|---|
| Granulated/crystalline nootkatone | 0.1-100 |
| Desiccant or salt | 0-99.9 |

Formulation C can be a powdered formulation or can be suspended as a slurry or dissolved in a suitable solution for liquid dispersal.

TABLE No. 5

Contemplated composition formulation D.

| Ingredient | Approximate Wt. % |
|---|---|
| Nootkatone | 0.1-10 |
| Cleaner | 90-99.9 |

The cleaner of composition of Formulation D above can be carpet powder, carpet shampoo, laundry detergent, hand soap, hand sanitizer, and the like. Carpet powders can include, for example, those sold under the brands of HARTZ®, THE ECOLOGY WORKS®, RESOLVE®, GLADE®, ARM & HAMMER®, DYSON®, and CARPET FRESH® brands. Carpet shampoos can include, for example, those sold under the brands of BISSELL®, FEBREEZE®, GLADE®, ARM & HAMMER®, ZEP®, and HOOVER® brands. Laundry detergents can include, for example, those sold under the brands of TIDE®, ALL®, GAIN®, WOOLITE®, ARM & HAMMER®, and WISK®.

Methods

According to some aspects of the current invention, nootkatone-containing compositions may be applied to dust mites directly or to surfaces, objects, or dust mite rich environments based on environmental conditions (such as raised humidity or temperature), seasonally (such as during summer), or in response to subjects displaying onset of symptoms consistent with an allergic response or asthma induced by dust mite allergens.

According to some aspects of the current invention, nootkatone-containing compositions may be applied to dust mites, surfaces, objects, or dust mite rich environments at any stage of the dust mite life cycle. According to some aspects of the current invention, nootkatone-containing compositions may be applied once per day or week, once per two weeks, once per month, once per two months, or once per three months.

Nootkatone-containing compositions can be applied by directly pouring the composition into water or placing a composition dispenser within a sink, bath, tank, washing machine, or any other appropriately sized receptacle such that the object or dust mite rich environment to be treated comes into contact with the nootkatone-containing composition at an effective concentration of nootkatone and/or an additional active ingredient, for example, between about 100 and about 2000 ppm, preferably between about 200 and about 400 ppm, most preferably about 300 ppm. The surface or dust mite rich environment to be treated may be exposed to any of the contemplated nootkatone-containing compositions for about 15 minutes to about 24 hours. In a preferred embodiment of one aspect of the current invention, the surface or dust mite rich environment to be treated is exposed to an effective amount of nootkatone, such as, at concentration of about 300 ppm, for about 15 to about 60 minutes.

In contrast to the many active agents against dust mites in the art, nootkatone is able in some compositions of the current invention to form a film on the surface of water. Therefore, some methods according to the current invention employ procedures of immersing an object or dust mite rich environment to be treated into a nootkatone-containing receptacle such that the object or dust mite rich environment to be treated must pass through the surface of the water such that a film of nootkatone at least partially envelopes the object or dust mite rich environment. For example, a pillow, stuffed toy, or bed mattress may be dipped into a composition containing nootkatone in a domestic bath.

In one embodiment, a method of treating or preventing a dust mite infestation includes providing a nootkatone-containing composition, optionally diluting the composition to a working concentration with a liquid carrier, and applying the composition to a surface. The surface may either be the surface to be treated or the surface of a dispenser.

In another embodiment, a method of treating or preventing a dust mite infestation includes applying a nootkatone-containing composition to a surface by a dispenser that concomitantly applies the composition to the surface and removes from the surface at least one of dust, dirt, dust mite food, a dust mite allergen, grease, oil, lint, animal hair, an odor, and a stain.

In a further embodiment, a method of treating or preventing a dust mite infestation includes applying a nootkatone-containing composition to a surface, waiting for a period of time, and cleaning the surface to remove at least one of dust, dirt, dust mite food, a dust mite allergen, grease, oil, lint, animal hair, an odor, and a stain. The surface can be cleaned with a vacuum, such as a hypoallergenic vacuum.

In a further embodiment, a method of treating or preventing a dust mite infestation includes applying a nootkatone-containing composition to a surface and treating the surface with ultraviolet (uv) light of 200-400 nm wavelength prior to or after application of the nootkatone-containing composition.

In another contemplated embodiment, a method for reducing the potential for or severity or frequency of allergic reaction to dust mites includes applying a nootkatone-containing composition to a surface, and cleaning the surface to remove dust mite allergens therefrom. For example, the surface can be cleaned with a hypoallergenic vacuum. In another example, the surface can be cleaned using a detergent or cleaner that removes residual oil.

In another embodiment, it is within the scope of the present disclosure that nootkatone-containing compositions can be formulated or mixed with, if desired, conventional inert diluents or extenders of the type usable in conventional pesticide formulations or compositions, e.g., conventional pesticide dispersible carrier vehicles such as gases, solutions, emulsions, suspensions, emulsifiable concentrates, spray powders, pastes, soluble powders, dusting agents, granules, foams, pastes, tablets, aerosols, natural and synthetic materials impregnated with active compounds, microcapsules, and formulations used with burning equipment, such as fumigating cartridges, fumigating cans, and fumigating coils, as well as ULV cold mist and warm mist formulations.

Dispensers

Compositions disclosed herein may be dispensed using one or more of a spray bottle, a brush, a dropper, a sponge, a soft-tipped marking device with reservoir, a pressurized dispenser, an aerosol can, a roll on bottle, a powder dispenser, a mop, a dust mop, a broom, a wipe, a tissue, a duster, a duster sheet, a wet wipe, a wet pad, a vacuum rotor, a steam cleaner, a lint brush, a paint brush, a paint roller, a washing machine, a clothes drier, a clothes iron, a clothes press, and other devices suitable for application to surfaces, objects, or dust mite rich environments. For example, surfaces, objects, or dust mite rich environments may be treated by spraying, dusting, scrubbing, mopping, sweeping, brushing, wiping, dipping, soaking, painting, vacuuming, steam cleaning, ironing, pressing, dry cleaning, and/or coating with a nootkatone-containing composition.

Additional dispensers include a passive dispenser where the nootkatone-containing composition is released from the device without input of energy to the device or an active dispenser where energy stored within or applied to the device either releases a pressurized composition or applies a force to the composition to dispense the composition. In one embodiment, active dispensers may be controlled by a timer, a remote control for on-demand dispensing, or a motion sensor, temperature sensor or humidity detector for automatic dispensing.

Another aspect of the current invention includes pretreatment of surfaces, objects or dust mite rich environments to dust mites taking up residence and/or increasing in population size. This may be accomplished by coating the surfaces, objects or dust mite rich environments with compositions that resist removal from the surface and contain an amount of a nootkatone, such as a paint, a clear coat, a wax, an oil, an adhesive, a resin, and combinations thereof. Another approach includes lining the surfaces, objects or dust mite rich environments with one or more nootkatone-impregnated materials, such as thermoplastic or thermoset sheets impregnated with nootkatone. For example, a nootkatone-impregnated sheet optionally impervious to transmission of dust mite and/or dust mite allergens may be used to at least partially enclose a bed mattress. A further approach is to construct the surfaces, objects, or dust mite rich environments with nootkatone-impregnated or nootkatone-coated materials, such as plastics, wood, cloth, textiles, composites, porous materials to prevent re-infestation. Such an approach is particularly suitable for construction of beds, sofas, mattresses, pillows, bedding, and chairs. These approaches can be used individually or in any combination.

EXAMPLES

The following is illustrative of specific embodiments of the invention, and various uses thereof, and is set forth for explanatory purposes only and is not taken as limiting the invention.

Example No. 1: Susceptibility of Dust Mites to Treatment with Nootkatone Formulations This example describes a laboratory bioassay in which groups of dust mites were exposed to a solution of the product to determine dust mite susceptibility to nootkatone.

The organisms obtained for testing are presented in Table No. 6.

TABLE No. 6

Experimental organisms.

| Name | Scientific name | Life stage/sex |
|---|---|---|
| Dust mite | *Dermataphagoides farinae* | Adult/mixed sex |

Treatment

One milliliter of a 1% (wt/vol) nootkatone in ethanol formulation was applied directly to 9 cm discs of filter paper by pipette. The filter papers were allowed to dry completely and were cut to the appropriate size prior to the start of the test. Pure ethanol was used as a control.

Test Container Design

Treated and untreated (ethanol-treated only) filter papers were cut into 2.5 inch (6.35 cm) squares and folded into envelopes to serve as containers for the test. Five replicates of 35 dust mites were tested per treatment. After the mites were placed inside, the openings were sealed using clips so that the mites could not escape.

Assessments

Dust mites were only observed after 72 hours post-introduction to the test containers, due to their small size, and the likelihood of loss of mites during handling. The dust mites were scored according to the following criteria:

Knockdown: cannot right itself when placed on its back or otherwise initiate directional movement, but still exhibits movement in the limbs with or without tactile stimulation; and Dead (mortality): exhibits no movement, even with tactile stimulation.

Results

Figure 2:
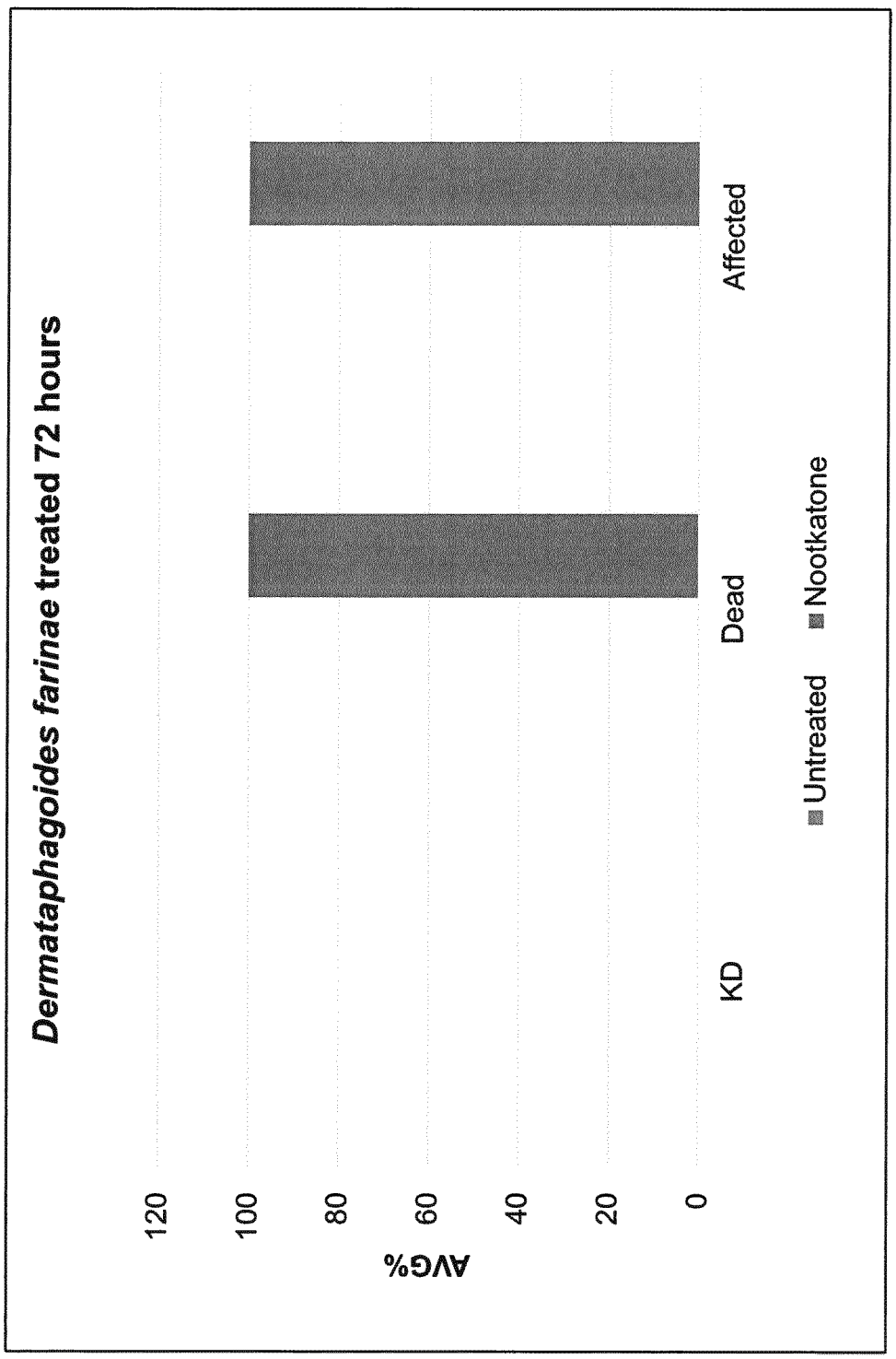
FIG. 2 illustrates percentages of knockdown (KD), dead, and affected dust mites after 72 hr treatment with a nootkatone-containing composition compared to an ethanol-only control.

Results of the test are shown in Table No. 7 and FIG. 2.

TABLE NO. 7

Treatment results.

| Time post introduction | Means | | | Standard Error | | |
|---|---|---|---|---|---|---|
| | KD | Dead | Affected | KD | Dead | Affected |
| Dust mites Untreated (ethanol only) | | | | | | |
| 72 hours | 0.0 | 0.0 | 0.0 | 0.0 | 0.0 | 0.0 |
| Nootkatone | | | | | | |
| 72 hours | 0.0 | 100.0 | 100.0 | 0.0 | 0.0 | 0.0 |

Five control replicates of 35 mites, or 175 total mites, were alive and unaffected after 72 hours of containment. In contrast, five replicates of 35 mites, or 175 total mites, were all dead after 72 hours of exposure to filter papers treated with 1% nootkatone in ethanol.

The test indicates 100% mortality rates of dust mites are achieved when dust mites are exposed to low concentrations of nootkatone. These results further demonstrate that ethanol did not contribute to the results seen with nootkatone, as the ethanol-only treated dust mites were unaffected.

Figure 3:
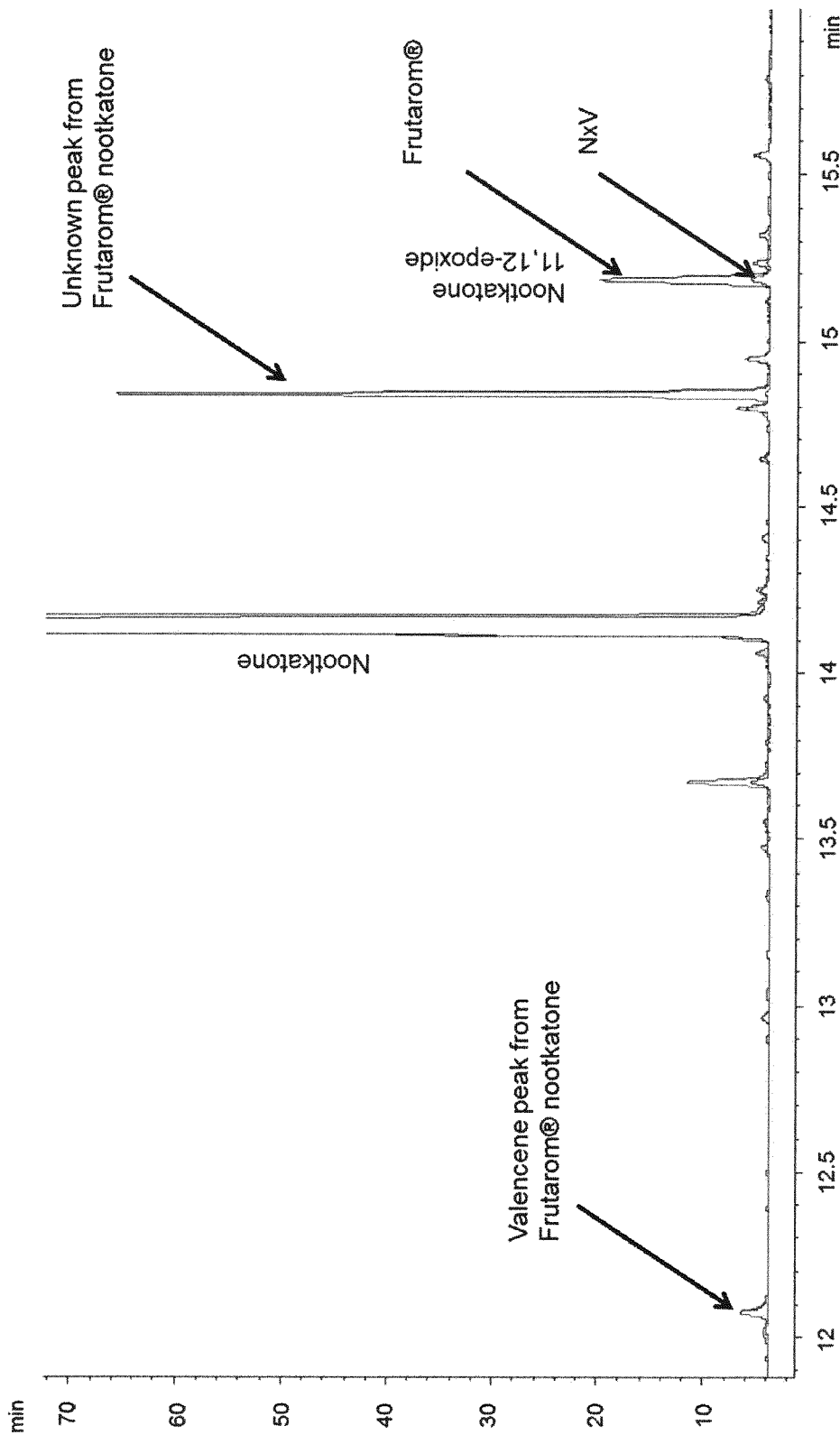
FIG. 3 is GC-FID chromatogram overlay of Frutarom® nootkatone (i.e., citrus-derived nootkatone) and the nootkatone (NxV) used for the dust mite studies described herein (see Examples below).
Figure 4:
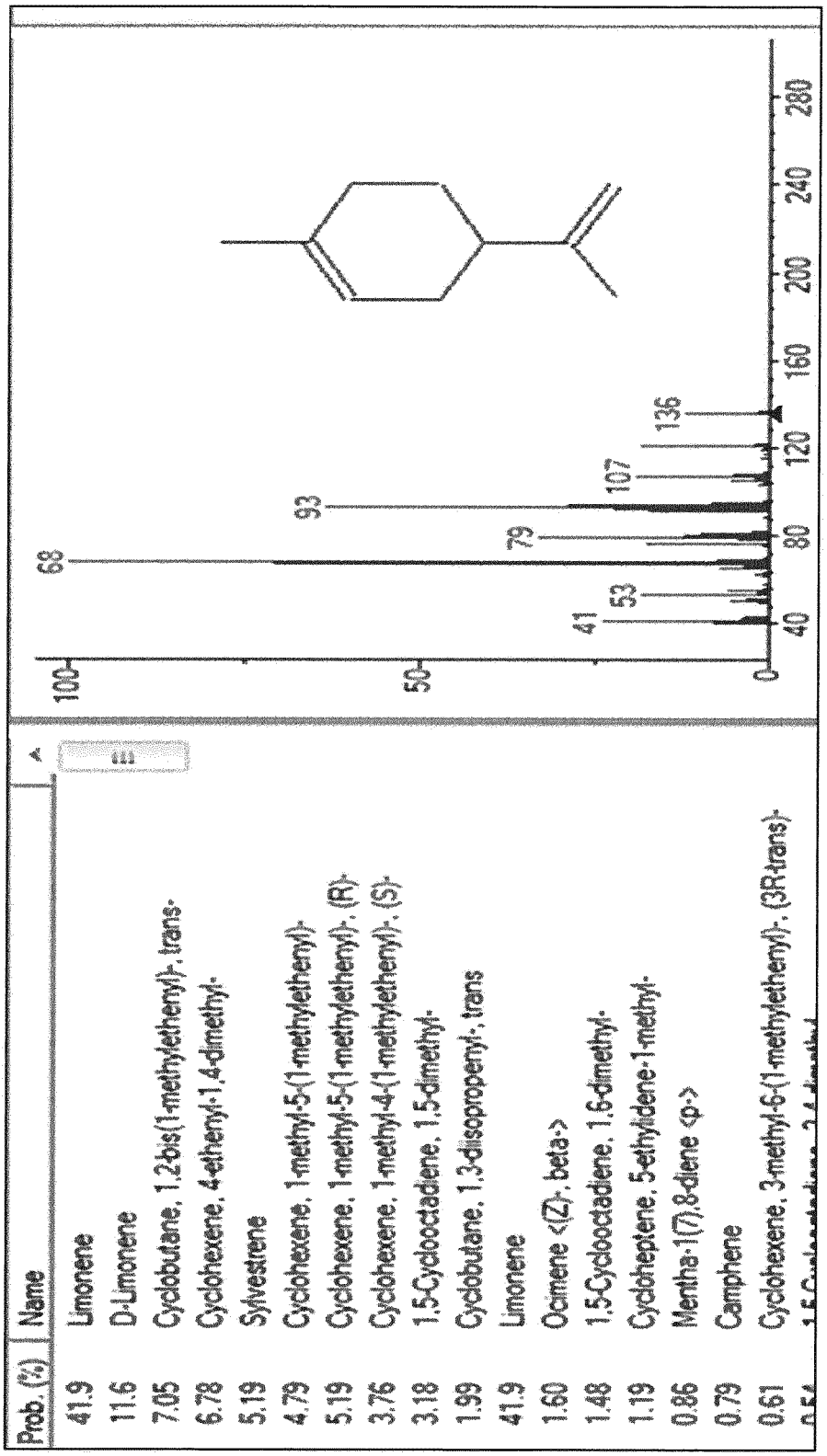
FIG. 4 is a GC-MS NIST library match of an unknown peak in Frutarom® nootkatone. The peak was identified as limonene. No limonene nor bergapten was found in the nootkatone used in the present application.

Example No. 2: Comparison of Fermentation-Derived Nootkatone with Citrus-Derived Nootkatone Overview Nootkatone, as defined herein, has a particular chemical profile indicative of its constituent chemical species. Other sources of nootkatone can have different chemical profiles and therefore actually represent different chemical compositions. GC-FID analyses of the nootkatone used in the studies described above (obtained from oxidation of fermentation-derived valencene, also known as, nootkatone ex valencene (NxV)) and a citrus fruit-derived nootkatone (also known as nootkatone ex citrus, which is derived from citrus fruit and available from Frutarom®, Corona, Calif.) are shown in FIG. 3. The nootkatone used in the studies described herein lacked valencene and demonstrated a lower amount of 11,12-epoxide than the Frutarom® nootkatone. Moreover, further analysis of an unknown peak from the Frutarom® nootkatone sample revealed that the Frutarom® sample contained limonene (see FIG. 4), whereas the nootkatone used in the present studies was limonene-free. These results underscore the different chemical profile of the nootkatone used herein (NxV) compared to commercially-available nootkatone derived from citrus, such as that provided by Frutarom®.

These results are also in accord with the observation (not shown) that nootkatone obtained from fermentation-derived valencene does not contain bergapten (or bergaptine). Bergapten (5-methoxypsoralen or 5-MOP) is a compound found in bergamot and citrus essential oils that causes phototoxicity in humans. (Gionfriddo et al. "Elimination of Furocoumarins in Bergamot Peel Oil," *Perfumer & Flavorist.*, 2004; 29:48-52; Ferreira Maia et al. "Plant-based insect repellents: a review of their efficacy, development and testing," Malaria Journal, 2011; 10:Suppl 1-11; and Kejlová et al. "Phototoxicity of bergamot oil assessed by in vitro techniques in combination with human patch tests." Toxicol In Vitro. 2007; 21:1298-1303). In addition, GHS health warning statements for bergapten indicate that it can cause allergic skin reactions, allergy or asthma symptoms, or breathing difficulties if inhaled, and can cause genetic defects or cancer in animals. For such reasons, a Cosmetic Ingredient Review expert panel in assessing the safety of 14 citrus-derived peel oil ingredients concluded no more than 0.0015% (15 ppm) bergapten should be included in cosmetic products (see "Safety Assessment of Citrus-Derived Peel Oils as Used in Cosmetics," Cosmetic Ingredient Review Expert Panel Final Report, Sep. 30, 2014: 1-31).

Bergapten is present in naturally derived valencene (from citrus) and carries over through the chemical oxidation that forms nootkatone. Bergapten can be photo-activated to become a skin irritant, which can be worse around an open bite wound. Therefore, bergapten-free nootkatone obtained from fermentation-derived valencene has particular advantages over plant-derived nootkatone and is preferable for topical application.

Example No 3 Production of Nootkatone Ex Valencene

Nootkatone ex valencene may be produced in vivo through expression of one or more enzymes involved in the nootkatone biosynthetic pathway in a recombinant yeast or in vitro using isolated, purified enzymes involved in the nootkatone biosynthetic pathway, such as those described in U.S. Patent Application Publication Nos. 2015/0007368 and 2012/0246767. The final conversion of valencene to nootkatone may be done enzymatically in vivo or in vitro, or may be performed by chemical oxidation (typically inorganic) in vitro.

Briefly, the valencene synthase gene (CVS) from *Citrus sinensis* cv. Valencia (Valencia orange) was cloned from RNA isolated from the juice vesicles of freshly harvested Valencia orange using the procedure previously described in Example 1 of U.S. Pat. No. 7,442,785.

First, Yep-GW-URA (Takahashi et al., (2007) *Biotechnol Bioeng*. 97(1):170-181) was generated by inserting a gateway cloning cassette (RfB) with the form attR1-$Cm^R$-ccdB gene-attR2 (Hartley et al., (2000) *Genome Res*. 10:1788-1795) into the SmaI restriction site of YEp352-URA (Bio-Technical Resources), which contains an URA3 selectable marker, an ADH1 promoter and an ADH1 terminator flanking, two BamHI sites (one 5' to the ADH1 promoter and the other 3' to the ADH terminator), a 2-micron ori, an ampicillin resistance gene and a colE1 origin of replication. The resulting vector was designated YEp-CVS-URA.

The CVS gene (set forth in SEQ ID NO: 1, and encoding amino acid sequence is set forth in SEQ ID NO: 2) was then amplified from RNA isolated from the juice vesicles of freshly harvested Valencia orange to contain restriction sites for subcloning into the yeast shuttle expression vector Yep-GW-URA. Following digestion of Yep-GW-URA with EcoRI and XbaI, the amplified product was cloned into the yeast shuttle expression vector YEp-GW-URA.

The YEp-CVS-ura vector was maintained in *S. cerevisiae* by selecting on SD minimal medium lacking uracil at 28° C. The vector also was maintained in *Escherichia coli* by selecting for resistance to ampicillin on LB medium containing 100 μg/mL ampicillin.

To screen for production of valencene, the *Saccharomyces cerevisiae* yeast cell strains CALI5-1 (ura3, leu2, his3, trp1, Δerg9::HIS3, HMG2cat/TRP1::rDNA, dpp1, sue), ALX7-95 (ura3, his3, trp1, Δerg9::HIS3, HMG2cat/TRP1::rDNA, dpp1, sue) or ALX11-30 (ura3, trp1, erg9def25, HMG2cat/TRP1::rDNA, dpp1, sue) were used.

The CALI5-1 strain (see U.S. published Appl. No. US20040249219; U.S. Pat. Nos. 6,531,303 and 6,689,593) has a Δleu2 deletion, which required the introduction of leucine into its media. ALX7-95 was derived from CALI5-1 by correcting the Aleut deficiency of CALI5-1 with a functional LEU2 gene (see U.S. published Appl. No. US2010/0151519).

ALX11-30 was constructed from CALI5-1 in several steps from ALX7-175.1 as described in US2010/0151519. Briefly, ALX7-95 HPS was obtained by transforming a plasmid containing the *Hyoscyamus muticus* premnaspirodiene synthase (HPS) into ALX7-95 strain. The YEp-HPS plasmid was obtained by cloning the gene for HPS into Yep-GW-URA to give YEp-HPS-ura (YEp-HPS). Then, an error prone PCR reaction of the ERGS gene was performed, and the resulting DNA was transformed into ALX7-95 harboring YEpHPS. Transformants were plated on YP medium lacking ergosterol and screened for premnaspirodiene production. Those that produced high levels of premnaspirodiene were saved. One strain, ALX7-168.25 [ura3, trp1, his3, $erg9^{def}$ 25, HMG2cat/TRP1::rDNA, dpp1, sue, YEpHPS] was transformed with a PCR fragment of the complete HIS3 gene to create a functional HIS3 gene. Transformants were isolated that were able to grow in the absence of histidine in the medium. From this transformation, ALX7-175.1 was isolated [ura3, trp1, erg9def25, HMG2cat/TRP1::rDNA, dpp1, sue YEpHPS]. Finally, the plasmid YEpHPS was removed by growing ALX7-175.1 several generations in YPD (10 g/L yeast extract, 20 g/L peptone, 20 g/L glucose) and plating cells on YPD plates. Colonies were identified that were unable to grow on SD medium without uracil (0.67 Bacto yeast nitrogen base without amino acids, 2% glucose, 0.14% yeast synthetic drop-out medium without uracil). This strain was designated ALX11-30.

For screening for production of valencene by valencene synthase or mutants, the YEp-CVS-ura plasmid, containing the CVS gene or modified versions of the CVS gene, was transformed into the above yeast strains using the lithium acetate yeast transformation kit (Sigma-Aldrich). The ALX7-95 and ALX11-30 strains generally produced more valencene than the CALI5-1 strain. CALI5-1 was used for initial screening in vials (as described in Example 3) and production in fermenters. Subsequently, ALX7-95 or ALX11-30 were used for screening in vials and fermenters. Typically, ALX7-95 was used for screening in vials and ALX11-30 was used for fermenters.

Transformants were selected on SDE-ura medium (0.67% Bacto yeast nitrogen base without amino acids, 2% glucose, 0.14% yeast synthetic drop-out medium supplement without uracil, and 40 mg/L ergosterol as needed). Colonies were picked and screened for valencene production using the microculture assay described below.

Production of valencene was performed in a 3-L fermentation tank (New Brunswick Bioflow 110). One liter of fermentation medium was prepared and autoclaved in the fermentation tank (20 g $(NH_4)_2SO_4$, 20 g $KH_2PO_4$, 1 g NaCl, $MgSO_4.7H_2O$, 4 g Solulys corn steep solids (Roquette)). The following components were then added: 20 ml mineral solution (0.028% $FeSO_4.7H_2O$, 0.029% $ZnSO_4.7H_2O$, 0.008% $CuSO_4.5H_2O$, 0.024% $Na_2MoO_4.2H_2O$, 0.024% $CoCl_2.6H_2O$, 0.017% $MnSO_4.H_2O$, 1 mL HCl); 10 mL 50% glucose; 30 mL vitamin solution (0.001% biotin: 0.012% calcium pantothenate, 0.06% inositol, 0.012% pyridoxine-HCl, 0.012% thiamine-HCl); 10 mL 10% $CaCl_2$, and 20 mL autoclaved soybean oil (purchased from local groceries). For sterol-requiring strains, including CALI5-1 and ALX7-95, 50 mg/L cholesterol or 40 mg/L ergosterol was included in the medium.

The seed culture for inoculating the fermentation medium was prepared by inoculating 50 mL of SDE-ura-trp medium (see Example 3.C.2.) with CALI5-1, ALX7-95 or ALX11-30 containing the YEp-CVS-ura plasmid. This culture was grown at 28° C. until early stationary phase (24-48 hr). One mL of this culture was inoculated into 500 mL of SDE-ura-trp medium and grown for 24 hr at 28° C. A 50-mL aliquot (5% inoculum) was used to inoculate the medium in the fermentation tank.

The fermentor was maintained at 28° C. The air flow was 1 vvm and the $dO_2$ was maintained above 30% by adjusting the agitation. The pH was maintained at 4.5 using phosphoric acid and NaOH or $NH_4OH$.

When the glucose concentration fell below 1 g/L, a feeding regimen was initiated such that the glucose in the fermentor was kept between 0 and 1 g/L. The glucose feed consisted of 60% glucose (w/v).

At the end of the fermentation, generally about 132 hours after inoculation, sodium sulfate was added to 10-15% final concentration as was an additional 50 mL soybean oil, and the contents of the fermentor were agitated for one hour. After allowing the fermentation vessel contents to settle, the oil was recovered by centrifugation and the valencene content in the oil was determined.

To assay valencene, 3 mL of suspension was placed in a vial to which 3 mL of acetone containing 20 mg/L cedrene was added. After vortexing, the mixture was extracted with 6 mL hexane containing 10 mg/L hexadecane followed by additional vortexing. The organic phase was transferred to a second vial for analysis by gas chromatography using cedrene and hexadecane as internal standards for extraction efficiency and injection, respectively. The CALI5-1, ALX7-95 or ALX11-30 *S. cerevisiae* containing Yep-CVS-ura, and expressing valencene synthase, was found to produce valencene.

The valencene-containing soybean oil, produced by fermentation as described above, was concentrated and purified using wiped-film distillation at 100° C. and 350 mTorr to generate an oil that contained approximately 68% valencene by weight. This material was converted to nootkatone by two different methods described below.

A. Oxidation of Valencene to Nootkatone Using Chromium Trioxide

The valencene distillate produced as described above was oxidized to nootkatone using chromium trioxide and pyridine in dicholoromethane as follows. Chromium trioxide (369 g, 3.69 mol, 22 eq) was added in portions to a solution of pyridine (584 g, 7.4 mol, 44 eq) in 5 L of dicholoromethane. The mixture was stirred for 10 minutes, 50 grams of valencene distillate (68% w/w, 0.167 mol, 1 eq) was added over four minutes, and the mixture was stirred at 22° C. for 18 hours. The liquor was drained from the vessel, and the solids were washed twice with 2 L of methyl tert-butyl ether (MTBE). The combined organic layers were further diluted with 2 L of MTBE and successively washed three times with 1.25 L of 5% sodium hydroxide, twice with 2 L of 5% hydrochloric acid, and once with 2 L of brine. The organic phase was dried over 200 grams of anhydrous sodium sulfate, filtered, and concentrated by evaporation to give 36.8 grams crude nootkatone (48% w/w, 0.081 mol, 48% yield).

B. Oxidation of Valencene to Nootkatone Using Silica Phosphonate-Immobilized Chromium (III) Catalyst Silica phosphonate chromium (III) resin (48.9 g, PhosphonicS, Ltd.) was placed in a 5 L round bottom flask equipped with a condenser, thermowell, overhead stirrer, and sparge tube. Two (2) L of t-butanol and valencene distillate (68%, 500 g, 1.67 moles, 1 eq) were added, the contents were heated to 45° C., and the heterogeneous suspension was allowed to stir as oxygen was sparged through the solution (ca 1.5 L/min) and nitrogen flushed over the head-space. 70% t-butyl hydroperoxide in water (TBHP, 315 g, 2.45 moles, 1.47 eq) was added to the solution over 2 hrs while the temperature of the reaction was heated and maintained at 60±5° C. The reaction was allowed to stir until >90%© of the valencene was consumed, as determined by gas chromatography. The reaction was then allowed to cool to room temperature and the silica catalyst removed by filtration. The flask and resin were washed with 500 mL isopropanol. One (1) L of deionized water was added to the combined organic solution (t-butanol and isopropanol), and the mixture was concentrated under reduced pressure by evaporation to afford an amber colored oil. The oil was dissolved in 3 L of toluene and washed with 3.125 L of 15% sulfuric acid for 15 minutes with vigorous agitation. The aqueous layer was removed and re-extracted with 1 L of toluene. The combined toluene layers were then washed three times with 2.5 L of 1 M sodium hydroxide, twice with 500 mL saturated sodium chloride, and dried over anhydrous magnesium sulfate. After filtration, the solvent was removed under reduced pressure by evaporation to afford 378 g of viscous amber oil (33% nootkatone by weight, 0.57 moles, 34% yield).

Sequence Listing:
(Citrus valencene synthase)
SEQ ID NO: 1 atgtcgtctggagaaacatttcgtcctactgcagatttccatcctagtt tatggagaaaccatttcctcaaaggtgcttctgatttcaagacagttga tcatactgcaactcaagaacgacacgaggcactgaaagaagaggtaagg agaatgataacagatgctgaagataagcctgttcagaagttacgcttga ttgatgaagtacaacgcctgggggtggcttatcactttgagaaagaaat agaagatgcaatacaaaaattatgtccaatctatattgacagtaataga gctgatctccacaccgtttcccttcattttcgattgcttaggcagcaag gaatcaagatttcatgtgatgtgtttgagaagttcaaagatgatgaggg tagattcaagtcatcgttgataaacgatgttcaagggatgttaagtttg tacgaggcagcatacatggcagttcgcggagaacatatattagatgaag ccattgctttcactaccactcacctgaagtcattggtagctcaggatca tgtaaccctaagcttgcggaacagataaatcatgctttataccgtcct cttcgtaaaaccctaccaagattagaggcgaggtattttatgtccatga tcaattcaacaagtgatcatttatacaataaaactctgctgaattttgc aaagttagattttaacatattgctagagctgcacaaggaggaactcaat gaattaacaaagtggtggaaagatttagacttcactacaaaactacctt atgcaagagacagattagtggagttatattttttgggatttagggacata cttcgagcctcaatatgcatttgggagaaagataatgacccaattaaat tacatattatccatcatagatgatacttatgatgcgtatggtacacttg aagaactcagcctctttactgaagcagttcaaagatggaatattgaggc cgtagatatgcttccagaatacatgaaattgatttacaggacactctta gatgcttttaatgaaattgaggaagatatggccaagcaaggaagatcac actgcgtacgttatgcaaaagaggagaatcaaaaagtaattggagcata ctctgttcaagccaaatggttcagtgaaggttacgttccaacaattgag gagtatatgcctattgcactaacaagttgtgcttacacattcgtcataa caaattccttccttggcatgggtgattttgcaactaaagaggttttga atggatctccaataaccctaaggttgtaaaagcagcatcagttatctgc agactcatggatgacatgcaaggtcatgagtttgaggagaagagaggac atgttgcgtcagctattgaatgttacacgaagcagcatggtgtctctaa ggaagaggcaattaaaatgtttgaagaagaagttgcaaatgcatggaaa gatattaacgaggagttgatgatgaagccaaccgtcgttgcccgaccac tgctcgggacgattcttaatcttgctcgtgcaattgattttatttacaa agaggacgacggctatacgcattcttacctaattaaagatcaaattgct tctgtgctaggagaccacgttccattttga (Citrus valencene synthase)
SEQ ID NO: 2
MSSGETFRPTADFHPSLWRNHFLKGASDFKTVDHTATQERHEALKEEVR

RMITDAEDKPVQKLRLIDEVQRLGVAYHFEKEIEDAIQKLCPIYIDSNR

-continued

ADLHTVSLHFRLLRQQGIKISCDVFEKFKDDEGRFKSSLINDVQGMLSL

YEAAYMAVRGEHILDEAIAFTTTHLKSLVAQDHVTPKLAEQINHALYRP

LRKTLPRLEARYFMSMINSTSDHLYNKTLLNFAKLDFNILLELHKEELN

ELTKWWKDLDFTTKLPYARDRLVELYFWDLGTYFEPQYAFGRKIMTQLN

YILSIIDDTYDAYGTLEELSLFTEAVQRWNIEAVDMLPEYMKLIYRTLL

DAFNEIEEDMAKQGRSHCVRYAKEENQKVIGAYSVQAKWFSEGYVPTIE

EYMPIALTSCAYTFVITNSFLGMGDFATKEVFEWISNNPKVVKAASVIC

RLMDDMQGHEFEQKRGHVASAIECYTKQHGVSKEEAIKMFEEEVANAWK

-continued

DINEELMMKPTVVARPLLGTILNLARAIDFIYKEDDGYTHSYLIKDQIA

SVLGDHVPF

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention. Percentages disclosed herein may otherwise vary in amount by ±10, 20, or 30% from values disclosed herein.

What is claimed is:

1. A method of treating or preventing a dust mite infestation comprising:
    (a) providing a nootkatone-containing composition, wherein the nootkatone is nootkatone ex valencene, wherein the nootkatone ex valencene is limonene-free and bergapten-free, and wherein the nootkatone-containing composition is limonene-free and bergapten-free;
    (b) optionally reducing the concentration of the composition to a working concentration with a carrier;
    (c) applying an effective amount of the composition to a surface; and
    (d) killing or repelling dust mites on the surface,
    wherein the composition has a reduced risk for causing allergy or asthma symptoms or breathing difficulties if inhaled compared to a composition comprising nootkatone that is neither limonene-free nor bergapten-free, and
    wherein the dust mite infestation comprises dust mites of the genus *Dermatophagoides*.

2. The method of claim 1, wherein the surface is either the surface to be treated or a surface of a dispenser.

3. The method of claim 1, wherein the carrier is a liquid or a powder.

4. The method of claim 1, wherein the nootkatone-containing composition is a concentrate.

5. The method of claim 1, wherein the nootkatone-containing composition is applied to the surface using a dispenser, and wherein the dispenser concomitantly applies the composition to the surface and removes from the surface at least one of dust, dirt, dust mite food, a dust mite allergen, grease, oil, lint, animal hair, an odor, or a stain.

6. The method of claim 5, wherein the dispenser is a brush, a sponge, a soft-tipped marking device with reservoir, a pressurized dispenser, an aerosol can, a roll on bottle, a mop, a dust mop, a broom, a wipe, a tissue, a duster, a duster sheet, a wet wipe, a wet pad, a vacuum rotor, a steam cleaner, a lint brush, a paint brush, a paint roller, a washing machine, or a clothes drier.

7. The method of claim 1 further comprising:
    (e) cleaning the surface to remove at least one of dust, dirt, dust mite food, a dust mite allergen, grease, oil, lint, animal hair, an odor, or a stain from the surface.

8. The method of claim 7, wherein step (c) is first performed and a period of time is allowed to pass before step (e) is performed.

9. The method of claim 8 further comprising (f) reapplying the nootkatone-containing composition to the surface after step (e) is performed.

10. The method of claim 8, wherein the period of time is a minute, an hour, a day, or any multiple thereof.

11. The method of claim 7 further comprising treating the surface with ultraviolet (uv) light of 200-400 nm wavelength.

12. The method of claim 11, wherein the surface is treated with uv light for a period of a minute, an hour, or a day.

13. The method of claim 11, wherein treating the surface with uv light of 200-400 nm wavelength is performed before applying the nootkatone-containing composition to the surface.

14. The method of claim 7, wherein the surface is cleaned with a vacuum.

15. The method of claim 1, wherein the nootkatone-containing composition comprises:
(a) about 0.1% to about 10% wt/vol nootkatone;
(b) about 0.1% to about 10% wt/vol benzyl benzoate; and
(c) about 80% to about 99.8% carrier.

16. The method of claim 1, wherein the nootkatone-containing composition contains about 0.01% to at or about 5% nootkatone by weight of the composition.

17. The method of claim 16, wherein step (b) is not performed.

18. The method of claim 1, wherein the composition is applied to the surface to obtain an effective nootkatone concentration of about 0.16 mg/cm$^2$.

* * * * *

SEQUENCE LISTING

<160> NUMBER OF SEQ ID NOS: 2

<210> SEQ ID NO 1
<211> LENGTH: 1647
<212> TYPE: DNA
<213> ORGANISM: Citrus sinensis

<400> SEQUENCE: 1

| | | | | | |
|---|---|---|---|---|---|
| atgtcgtctg | gagaaacatt | tcgtcctact | gcagatttcc | atcctagttt atggagaaac | 60 |
| catttcctca | aaggtgcttc | tgatttcaag | acagttgatc | tatactgcaac tcaagaacga | 120 |
| cacgaggcac | tgaaagaaga | ggtaaggaga | atgataacag | atgctgaaga taagcctgtt | 180 |
| cagaagttac | gcttgattga | tgaagtacaa | cgcctggggg | tggcttatca ctttgagaaa | 240 |
| gaaatagaag | atgcaataca | aaaattatgt | ccaatctata | ttgacagtaa tagagctgat | 300 |
| ctccacaccg | tttcccttca | ttttcgattg | cttaggcagc | aaggaatcaa gatttcatgt | 360 |
| gatgtgtttg | agaagttcaa | agatgatgag | ggtagattca | agtcatcgtt gataaacgat | 420 |
| gttcaaggga | tgttaagttt | gtacgaggca | gcatacatgg | cagttcgcgg agaacatata | 480 |
| ttagatgaag | ccattgcttt | cactaccact | cacctgaagt | cattggtagc tcaggatcat | 540 |
| gtaacccta | agcttgcgga | acagataaat | catgctttat | accgtcctct tcgtaaaacc | 600 |
| ctaccaagat | tagaggcgag | gtattttatg | tccatgatca | attcaacaag tgatcattta | 660 |
| tacaataaaa | ctctgctgaa | ttttgcaaag | ttagatttta | acatattgct agagctgcac | 720 |
| aaggaggaac | tcaatgaatt | aacaaagtgg | tggaaagatt | tagacttcac tacaaaacta | 780 |
| ccttatgcaa | gagacagatt | agtggagtta | tattttggg | atttagggac atacttcgag | 840 |
| cctcaatatg | catttgggag | aaagataatg | acccaattaa | attacatatt atccatcata | 900 |
| gatgatactt | atgatgcgta | tggtacactt | gaagaactca | gcctctttac tgaagcagtt | 960 |
| caaagatgga | atattgaggc | cgtagatatg | cttccagaat | acatgaaatt gatttacagg | 1020 |
| acactcttag | atgcttttaa | tgaaattgag | gaagatatgg | ccaagcaagg aagatcacac | 1080 |
| tgcgtacgtt | atgcaaaaga | ggagaatcaa | aaagtaattg | gagcatactc tgttcaagcc | 1140 |
| aaatggttca | gtgaaggtta | cgttccaaca | attgaggagt | atatgcctat tgcactaaca | 1200 |
| agttgtgctt | acacattcgt | cataacaaat | tccttccttg | gcatgggtga ttttgcaact | 1260 |
| aaagaggttt | ttgaatggat | ctccaataac | cctaaggttg | taaaagcagc atcagttatc | 1320 |
| tgcagactca | tggatgacat | gcaaggtcat | gagtttgagc | agaagagagg acatgttgcg | 1380 |
| tcagctattg | aatgttacac | gaagcagcat | ggtgtctcta | aggaagaggc aattaaaatg | 1440 |
| tttgaagaag | aagttgcaaa | tgcatggaaa | gatattaacg | aggagttgat gatgaagcca | 1500 |

```
accgtcgttg cccgaccact gctcgggacg attcttaatc ttgctcgtgc aattgatttt    1560
atttacaaag aggacgacgg ctatacgcat tcttacctaa ttaaagatca aattgcttct    1620
gtgctaggag accacgttcc attttga                                         1647
```

<210> SEQ ID NO 2
<211> LENGTH: 548
<212> TYPE: PRT
<213> ORGANISM: Citrus sinensis

<400> SEQUENCE: 2

```
Met Ser Ser Gly Glu Thr Phe Arg Pro Thr Ala Asp Phe His Pro Ser
1               5                   10                  15

Leu Trp Arg Asn His Phe Leu Lys Gly Ala Ser Asp Phe Lys Thr Val
            20                  25                  30

Asp His Thr Ala Thr Gln Glu Arg His Glu Ala Leu Lys Glu Val
        35                  40                  45

Arg Arg Met Ile Thr Asp Ala Glu Asp Lys Pro Val Gln Lys Leu Arg
50                  55                  60

Leu Ile Asp Glu Val Gln Arg Leu Gly Val Ala Tyr His Phe Glu Lys
65                  70                  75                  80

Glu Ile Glu Asp Ala Ile Gln Lys Leu Cys Pro Ile Tyr Ile Asp Ser
                85                  90                  95

Asn Arg Ala Asp Leu His Thr Val Ser Leu His Phe Arg Leu Leu Arg
            100                 105                 110

Gln Gln Gly Ile Lys Ile Ser Cys Asp Val Phe Glu Lys Phe Lys Asp
        115                 120                 125

Asp Glu Gly Arg Phe Lys Ser Ser Leu Ile Asn Asp Val Gln Gly Met
130                 135                 140

Leu Ser Leu Tyr Glu Ala Ala Tyr Met Ala Val Arg Gly Glu His Ile
145                 150                 155                 160

Leu Asp Glu Ala Ile Ala Phe Thr Thr Thr His Leu Lys Ser Leu Val
                165                 170                 175

Ala Gln Asp His Val Thr Pro Lys Leu Ala Glu Gln Ile Asn His Ala
            180                 185                 190

Leu Tyr Arg Pro Leu Arg Lys Thr Leu Pro Arg Leu Glu Ala Arg Tyr
        195                 200                 205

Phe Met Ser Met Ile Asn Ser Thr Ser Asp His Leu Tyr Asn Lys Thr
210                 215                 220

Leu Leu Asn Phe Ala Lys Leu Asp Phe Asn Ile Leu Leu Glu Leu His
225                 230                 235                 240

Lys Glu Glu Leu Asn Glu Leu Thr Lys Trp Trp Lys Asp Leu Asp Phe
                245                 250                 255

Thr Thr Lys Leu Pro Tyr Ala Arg Asp Arg Leu Val Glu Leu Tyr Phe
            260                 265                 270

Trp Asp Leu Gly Thr Tyr Phe Glu Pro Gln Tyr Ala Phe Gly Arg Lys
        275                 280                 285

Ile Met Thr Gln Leu Asn Tyr Ile Leu Ser Ile Ile Asp Asp Thr Tyr
290                 295                 300

Asp Ala Tyr Gly Thr Leu Glu Glu Leu Ser Leu Phe Thr Glu Ala Val
305                 310                 315                 320

Gln Arg Trp Asn Ile Glu Ala Val Asp Met Leu Pro Glu Tyr Met Lys
                325                 330                 335

Leu Ile Tyr Arg Thr Leu Leu Asp Ala Phe Asn Glu Ile Glu Glu Asp
```

-continued

```
                        340                 345                 350
Met Ala Lys Gln Gly Arg Ser His Cys Val Arg Tyr Ala Lys Glu Glu
        355                 360                 365

Asn Gln Lys Val Ile Gly Ala Tyr Ser Val Gln Ala Lys Trp Phe Ser
        370                 375                 380

Glu Gly Tyr Val Pro Thr Ile Glu Glu Tyr Met Pro Ile Ala Leu Thr
385                     390                 395                 400

Ser Cys Ala Tyr Thr Phe Val Ile Thr Asn Ser Phe Leu Gly Met Gly
                405                 410                 415

Asp Phe Ala Thr Lys Glu Val Phe Glu Trp Ile Ser Asn Asn Pro Lys
                420                 425                 430

Val Val Lys Ala Ala Ser Val Ile Cys Arg Leu Met Asp Asp Met Gln
        435                 440                 445

Gly His Glu Phe Glu Gln Lys Arg Gly His Val Ala Ser Ala Ile Glu
        450                 455                 460

Cys Tyr Thr Lys Gln His Gly Val Ser Lys Glu Glu Ala Ile Lys Met
465                 470                 475                 480

Phe Glu Glu Glu Val Ala Asn Ala Trp Lys Asp Ile Asn Glu Glu Leu
                485                 490                 495

Met Met Lys Pro Thr Val Val Ala Arg Pro Leu Leu Gly Thr Ile Leu
                500                 505                 510

Asn Leu Ala Arg Ala Ile Asp Phe Ile Tyr Lys Glu Asp Asp Gly Tyr
                515                 520                 525

Thr His Ser Tyr Leu Ile Lys Asp Gln Ile Ala Ser Val Leu Gly Asp
        530                 535                 540

His Val Pro Phe
545
```